US012023499B2

(12) United States Patent
Towe (10) Patent No.: US 12,023,499 B2
(45) Date of Patent: Jul. 2, 2024

(54) METHODS AND SYSTEMS FOR MEASURING TISSUE IMPEDANCE AND MONITORING PVD TREATMENT USING NEURO-IMPLANTS WITH IMPROVED ULTRASOUND POWERING

(71) Applicant: Bruce C. Towe, Mesa, AZ (US)

(72) Inventor: Bruce C. Towe, Mesa, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 680 days.

(21) Appl. No.: 17/153,441

(22) Filed: Jan. 20, 2021

(65) Prior Publication Data

US 2021/0138242 A1    May 13, 2021

Related U.S. Application Data

(63) Continuation of application No. 15/126,844, filed as application No. PCT/US2015/020956 on Mar. 17, 2015, now abandoned.
(Continued)

(51) Int. Cl.
*A61N 1/36* (2006.01)
*A61B 5/00* (2006.01)
(Continued)

(52) U.S. Cl.
CPC .......... *A61N 1/3606* (2013.01); *A61B 5/0538* (2013.01); *A61B 5/4836* (2013.01);
(Continued)

(58) Field of Classification Search
CPC .............. A61N 1/3606; A61N 1/36128; A61N 1/3787; A61N 7/00; A61B 5/0538;
(Continued)

(56) References Cited

U.S. PATENT DOCUMENTS

| 3,735,756 A | 5/1973 | Richards et al. |
| 3,971,365 A | 7/1976 | Smith |

(Continued)

FOREIGN PATENT DOCUMENTS

| EP | 0576543 | 5/2000 |
| KR | 20-0391529 | 8/2005 |

(Continued)

OTHER PUBLICATIONS

Abdo et al.: "Feasibility of Neural Stimulation With Floating-Light-Activated Microelectrical Stimulators", IEEE Trans. Biomed. Cir. Systems, vol. 5, No. 2., pp. 179-188, Apr. 2011.

(Continued)

Primary Examiner — Eric F Winakur
(74) Attorney, Agent, or Firm — Norton Rose Fulbright US LLP (57) ABSTRACT

Methods and systems for measuring tissue impedance and monitoring PVD treatment using neuro-implants with improved wireless powering are disclosed. In some embodiments, an implanted device including a wireless energy receiver, a demodulation circuit, and electrodes may be configured to received modulated energy from an energy transmitter. The implanted device may convert the energy to an electrical voltage to be applied to tissue to adjust the tissue's impedance. The tissue impedance may be measured with a computing system by receiving and processing an energy signal emitted/produced in response to the electrical voltage applied by the implanted device. In some embodiments, improved microwave powering schemes may be utilized to power the implanted device. In some embodiments, improved ultrasound powering schemes may be utilized to power the implanted device. For example, energy transfer efficiency from different transmitters may be evalu- (Continued)

ated to select for energy transmission the transmitter that yields optimal energy transfer efficiency.

14 Claims, 6 Drawing Sheets

Related U.S. Application Data (60) Provisional application No. 61/954,064, filed on Mar. 17, 2014, provisional application No. 62/042,685, filed on Aug. 27, 2014, provisional application No. 62/043,774, filed on Aug. 29, 2014.

(51) Int. Cl.
    *A61B 5/0538*      (2021.01)
    *A61N 1/378*      (2006.01)
    *A61N 7/00*      (2006.01)

(52) U.S. Cl.
    CPC .......... *A61B 5/7228* (2013.01); *A61B 5/7271* (2013.01); *A61N 1/36128* (2013.01); *A61N 1/3787* (2013.01); *A61N 7/00* (2013.01); *A61B 2560/0219* (2013.01); *A61N 2007/0004* (2013.01)

(58) Field of Classification Search
    CPC ... A61B 5/4836; A61B 5/7228; A61B 5/7271; A61B 2007/0004
    See application file for complete search history.

(56) References Cited

U.S. PATENT DOCUMENTS

| | | | |
|---|---|---|---|
| 4,057,069 | A | 11/1977 | Oorffer et al. |
| 4,289,134 | A | 9/1981 | Bernstein |
| 4,679,572 | A | 7/1987 | Baker |
| 4,706,681 | A | 11/1987 | Breyer et al. |
| 4,901,084 | A | 2/1990 | Huguenin et al. |
| 5,076,278 | A | 12/1991 | Vilkomersen et al. |
| 5,466,348 | A | 11/1995 | Holm-Kennedy |
| 5,733,281 | A | 3/1998 | Nardella |
| 6,239,724 | B1 | 5/2001 | Doron et al. |
| 6,409,684 | B1 | 6/2002 | Wilk |
| 6,520,911 | B1 | 2/2003 | Wen |
| 6,647,296 | B2 | 11/2003 | Fischell et al. |
| 6,772,490 | B2 | 8/2004 | Toda |
| 7,024,248 | B2 | 4/2006 | Penner et al. |
| 7,174,037 | B2 | 2/2007 | Arnone et al. |
| 7,702,395 | B2 | 4/2010 | Towe et al. |
| 8,340,773 | B2 | 12/2012 | Towe et al. |
| 8,369,956 | B2 | 2/2013 | Towe et al. |
| 8,649,875 | B2 * | 2/2014 | Sarvazyan ......... A61N 1/36062 607/60 |
| 2002/0169354 | A1 | 11/2002 | Munro |
| 2002/0193840 | A1 | 12/2002 | Sawan et al. |
| 2004/0068204 | A1 | 4/2004 | Lmran et al. |
| 2006/0079936 | A1 | 4/2006 | Boveja et al. |
| 2006/0161225 | A1 | 7/2006 | Sormann et al. |
| 2007/0006653 | A1 | 1/2007 | Kim |
| 2007/0027508 | A1 | 2/2007 | Cowan |
| 2007/0185551 | A1 | 8/2007 | Meadows et al. |
| 2007/0293910 | A1 | 12/2007 | Strother et al. |
| 2008/0077188 | A1 | 3/2008 | Denker |
| 2008/0086036 | A1 | 4/2008 | Hartley et al. |
| 2008/0108915 | A1 | 5/2008 | Penner |
| 2008/0188909 | A1 | 8/2008 | Bradley |
| 2008/0208293 | A1 | 8/2008 | Parramon et al. |
| 2008/0215112 | A1 | 9/2008 | Firlik et al. |
| 2008/0306359 | A1 | 12/2008 | Zdeblick et al. |
| 2010/0161007 | A1 | 6/2010 | King |
| 2010/0234924 | A1 | 9/2010 | Willis |
| 2012/0041310 | A1 | 2/2012 | Towe |
| 2012/0041499 | A1 | 2/2012 | Towe |
| 2012/0197342 | A1 | 8/2012 | Towe |
| 2012/0316454 | A1 | 12/2012 | Carter |

FOREIGN PATENT DOCUMENTS

| | | |
|---|---|---|
| WO | WO1999/006108 | 2/1999 |
| WO | WO2003/107372 | 12/2003 |
| WO | WO2004/069129 | 8/2004 |
| WO | WO2004/105583 | 12/2004 |
| WO | WO2005/120203 | 12/2005 |
| WO | WO2009/055594 | 4/2009 |
| WO | WO2010/027963 | 3/2010 |
| WO | WO2010/135634 | 11/2010 |
| WO | WO2011/156495 | 12/2011 |

OTHER PUBLICATIONS

Ben-Haim: "A new nonfluroscopic electroanatomical mapping system," PACE, vol. 19, part II, pp. 709, Apr. 1996, (Abstract).

Borna et al.: "A Low-Power, Low-Voltage, User-Programmable, Wireless Interface for Reliable Neural Recording", 2011 IEEE Biomedical Circuits and Systems Conference (BioCAS), pp. 77-81, Nov. 2011.

Chestek et al.: "HermesC: Low-Power Wireless Neural Recording System for Freely Moving Primates", IEEE Transactions on Neural Systems and Rehabilitation Engineering, vol. 17, No. 4, pp. 330-338, 2009.

Dehennis et al.: "A Double-Sided Single-Chip Wireless Pressure Sensor," 15th IEEE Intl. Conf. on Micro Electro Mech. Sys., pp. 252-255, 2002.

Denisov et al.: "Ultrasonic vs. Inductive Power Delivery for Miniature Biomedical Implants," 2010 International Conference on Body Sensor Networks (BSN), pp. 84-89, 2010.

Gavrilov et al.: "Stimulation of human peripheral neural structures by focused ultrasound," Soviet Physics Acoustics-USSR, vol. 19.4, pp. 332-334, 1974.

Gepstein et al: "A Novel Method for Nonfluoroscopic Catheter-Based Electroanatomical Mapping of the Heart: In Vitro and In Vivo Accuracy Results," American Heart Association—Circulation 95, 1997.

Glenn et al.: "Electrical Stimulation of Excitable Tissue by Radio-Frequency Transmission," Annals of Surgery, vol. 150, No. 3, pp. 338-350, 1954.

Gulick et al.: "Characterization of Simple Wireless Neurostimulators and Sensors" 2014 36th Annual International Conference of the IEEE Engineering in Medicine and Biology Society, pp. 3130-3133, 2014.

Harpster et al.: "A Passive Wireless Integrated Humidity Sensor," Sensors Actuators A 95, pp. 100-107, 2002.

Heetderks: "RF Powering of Millimeter- and Submillimeter-Sized Neural Prosthetic Implants," IEEE Transactions on Biomedical Engineering, vol. 35, vo. 5, pp. 323-327, 1988.

Hu et al.: "Effects of Low-Intensity Ultrasound on the Central Nervous System of Primates," Aviation, Space, and Environmental Medicine, vol. 47.6, pp. 640-643, 1976.

Huber et al.: "Spinal Cord Stimulation in Severe, Inoperable Peripheral Vascular Disease," International Neuromodulation Society, vol. 3, No. 3, pp. 131-143, 2000.

International Preliminary Report on Patentability for PCT Application No. PCT/US2011/039642, dated Dec. 10, 2012.

International Preliminary Report on Patentability for PCT Application No. PCT/US2011/049966, dated Mar. 14, 2013.

International Preliminary Report on Patentability for PCT Application No. PCT/US09/55594, dated Mar. 8, 2011.

International Preliminary Report on Patentability for PCT Application No. PCT/US2004/016417, dated Jan. 19, 2005.

International Preliminary Report on Patentability for PCT Application No. PCT/US2008/080994, dated Apr. 27, 2010.

International Search Report and Written Opinion for PCT Application No. PCT/US2010/035753, dated Dec. 1, 2011.

International Search Report and Written Opinion for PCT Application No. PCT/US2015/020956, dated Sep. 4, 2015.

(56) References Cited

OTHER PUBLICATIONS

Khalil et al.: "Effects of Aging on Neurogenic Vasodilator Responses Evoked by Transcutaneous Electrical Nerve Stimulation: Relevance to Wound Healing," Journal of Gerontology, vol. 55A, No. 6: pp. 257-263, 2000.

Kun et al.: "Algorithm for Tissue Ischemia Estimation Based on Electrical Impedance Spectroscopy", IEEE Transactions on Biomedical Engineering, vol. 50, No. 2, pp. 1352-1359, 2003.

Larson et al.: "Miniature Ultrasonically Powered Wireless Nerve Cuff Stimulator", 5th International IEEE Conference on Neural Engineering , pp. 265-268, 2011.

Lewis et al.:"An ultrasonic approach to localization of fiducial markers for interactive, image-guided neurosurgery. I. Principles," IEEE Transactions on Biomedical Engineering, vol. 45, No. 5, pp. 620-630, 1998.

Lindsey et al.: "A New Technique for Transmission of Signals from Implantable Transducers," IEEE Trans. Biomed. Engineering, vol. 45, No. 5, pp. 614-619, 1998.

Loeb et al.: "BION™ system for distr. neural prosthetics," Medical Engineering & Physics, vol. 23, pp. 9-18, 2001.

Matthaei: "A Study of the Optimum Design of Wide-Band Parametric Amplifiers and Up-Converters", IRE Transactions on Microwave Theory and Techniques, pp. 23-28, Jan. 1961.

Mellert et al.: "Detection of (Reversible) Myocardial Ischemic Injury by Means of Electrical Bioimpedance", IEEE Transactions on Biomedical Engineering, vol. 58, No. 6, pp. 1511-1518, Jun. 2011.

Meyer et al.: "Application of Sonomicrometry and Multidimensional Scaling to Cardiac Catheter Tracking," IEEE Transactions on Biomedical Engineering, vol. 44, No. 11, pp. 1061-1067, 1997.

Mihran et al.: "Temporally-Specific Modification of Myelinated Axon Excitability In Vitro Following a Single Ultrasound Pulse." Ultrasound in Medicine & Biology, vol. 16, No. 3, pp. 297-309, 1990.

Minqui et al.: "Data Communication Between Brain Implants and Computer," IEEE Transactions on Neural Systems and Rehabilitation Engineering, vol. 11, No. 2, pp. 189-192, 2003.

Mohseni et al. "Wireless Multichannel Biopotential Recording Using an Integrated FM Telemetry Circuit", IEEE Transactions on Neural Systems and Rehabilitation Engineering, vol. 13, No. 3, pp. 263-271, 2005.

Mohseni et al.: "A 1.48-mW Low-Phase-Noise Analog Frequency Modulator for Wireless Biotelemetry", , IEEE Transactions on Biomedical Engineering, vol. 52, No. 5, pp. 938-943, 2005.

Neihart et al.: "Micropower Circuits for Bidirectional Wireless Telemetry in Neural Recording Applications," IEEE Transactions on Biomedical Engineering, vol. 52, No. 11, pp. 1950-1959, 2005.

Ozeri et al.: "Ultrasonic Transcutaneous Energy Transfer for Powering Implanted Devices," Ultrasonics, vol. 50, pp. 556-566, 2010.

Park et al.: "The Effect of Microcurrent Electrical Stimulation on the Foot Blood Circulation and Pain of Diabetic Neuropathy," Journal of Physical Therapy Science, vol. 23, pp. 515-518, 2011.

Phillips et al.: "An Ultrasonically-Driven Piezoelectric Neural Stimulator," Proceedings of the 25th Annual International Conference of the IEEE Engineering in Medicine and Biology Society, pp. 1983-1986, 2003.

Poon et al.: "Optimal Frequency for Wireless Power Transmission into Dispersive Tissue," EEE Transactions on Antennas and Propagation, vol. 58, No. 5, pp. 1739-1749, 2010.

Sard et al.: "A Positive Resistance Up-Converter for Ultra-Low-Noise Amplification," IEEE Transactions on Microwave Theory and Techniques, vol. MTT-14, No. 12, pp. 608-618,1966.

Schwartzman et al.: "Electrical Impedance Properties of Normal and Chronically Infarcted Left Ventricular Myocardium", Journal of Interventional Cardiac Electrophysiology, vol. 3, pp. 213-224, 1999.

Seoane et al.: "Brain Electrical Impedance at Various Frequencies: The Effect of Hypoxia", 26th Annual International Conference of the IEEE Engineering in Medicine and Biology Society (IEMBS), pp. 2322-2325, 2004.

Sun et al.: "Data Communication Between Brain Implants and Computer," IEEE Transactions on Neural Systems and Rehabilitation Engineering, vol. 11, No. 2, pp. 189-192, 2003.

Takagi et al.: "The Actions of Ultrasound on the Myelinated Nerve, The Spinal Cord and the Brain," The Japanese Journal of Physiology, vol. 10, No. 2, pp. 183-193, 1960.

Takahata et al.: "Stentenna: A Micromachined Antenna Stent for Wireless Monitoring of Implantable Microsensors," Proc. 25th Ann. Intl. Conf. IEEE Eng. Med. Biol. Soc., pp. 3360-3363, 2003.

Towe et al. "Wireless Microstimulators for Treatment of Peripheral Vascular Disease" 6th International IEEE/EMBS Conference on. IEEE Neural Engineering (NER), pp. 1145-1488, 2013.

Towe et al.: "A Microwave Powered Injectable Neurostimulator", 34th Annual International Conference of the IEEE EMBS, San Diego, Ca, USA, pp. 5006-5009, 2012.

Towe: "Passive Biotelemetry by Frequency Keying", IEEE Transactions on Biomedical Engineering, vol. BME-33, No. 10, pp. 905-909, 1986.

Towe: Passive Backscatter Biotelemetry for Neural Interfacing, 3rd Intl. IEEE EMBS Conf., pp. 144-147, 2007.

Velling at al.: "Modulation of the Functional State of the Brain With the Aid of Focused Ultrasonic Action," Neuroscience and Behavioral Physiology, vol. 18, No. 5, pp. 369-375, 1988.

Wise et al.: "Wireless Implantable Microsystems: High-Density Electronic Interfaces to the Nervous System," Proceedings of the IEEE, vol. 92, No. 1, pp. 76-97, Jan. 2004.

\* cited by examiner

METHODS AND SYSTEMS FOR MEASURING TISSUE IMPEDANCE AND MONITORING PVD TREATMENT USING NEURO-IMPLANTS WITH IMPROVED ULTRASOUND POWERING

CROSS-REFERENCE TO RELATED APPLICATIONS

This application is a continuation from U.S. application Ser. No. 15/126,844 filed Sep. 16, 2016 which is a national phase application under 35 U.S.C. § 371 of International Application No. PCT/US2015/020956 filed Mar. 17, 2015, which claims the benefit of U.S. Provisional Application No. 61/954,064 filed Mar. 17, 2014, U.S. Provisional Application No. 62/042,685 filed Aug. 27, 2014, and U.S. Provisional Application No. 62/043,774 filed Aug. 29, 2014. The entire contents of each of the disclosures is incorporated herein by reference without disclaimer.

FIELD OF THE DISCLOSURE

This disclosure relates to wireless electromagnetically- or ultrasound-powered biomedical sensors, and more particularly relates to wireless electromagnetically- or ultrasound-powered biomedical sensors for measuring tissue impedance and monitoring peripheral vascular disease (PVD) treatment.

BACKGROUND

Tissues and body fluids change their electrical characteristics in complex ways that reflect the tissue mechanical and physiologic status. The electrical characteristics and/or the changes in the electrical characteristics can provide diagnostic and prognostic tissue information to a physician. For example, changes in blood flow with the heart may cause changes in tissue impedance due to lower blood resistivity during systole passing though the region of electrical current flow. In addition, cardiac output and cardiac performance is sometimes estimated using electrical impedance techniques. Present noninvasive methods for acquiring the electrical characteristics require the placement of cumbersome electrodes on the skin over the chest region and relatively large and bulky external instrumentation. As a consequence, their use is very limited.

As another example, respiration causes inflation of the lungs with insulating air, so tissue impedance across the electrical path that includes parts of the lung will increase with inspiration. Common noninvasive methods of monitoring respiration include placing electrodes on the skin such that the current path passes through the lung region. Parameters such as respiration rate and lung volume changes can be monitored by observing impedance changes. However, this approach, too, is relatively cumbersome for long term monitoring and requires the undesirable use of skin bioelectrodes and associated wires connecting to a controller box.

Many other physiologic processes also modulate tissue impedance, such as cancer, body organ disorders, wound healing, aging, contraction of the muscles, or any process that produces distortion of physical shape. Thus, electrical impedance measurement can be a powerful technique for monitoring changes in biological tissues that are of medical or physiologic interest. However, conventional techniques for measuring the electrical characteristics, such as those described above, suffer from numerous drawbacks. For example, a primary limitation of impedance measurements for such applications is a lack of specificity. In addition, such sensors, if made wireless, require attachment to an electronic telemetry circuit that is relatively large compared to the needs of minimal invasiveness necessary for many types of medical utility. Such systems would also require two way telemetry communication systems so as to control the current flow within the implant and then telemeter back the resulting current data, which would make the implant more invasive and too large for most applications. Even further, batteries or inductive power schemes tend to make implants relatively large compared to something that might be injected with minimal trauma.

BRIEF SUMMARY

Thus, there is a need for real-time measurement of tissue electrical impedance characteristics by minimally invasive methods so that important diagnostic and prognostic information may thereby be obtained. Accordingly, the present disclosure includes methods and apparatuses for measuring tissue impedance and monitoring PVD treatment using neuro-implants with improved ultrasound powering. Embodiments include the use of microwave energy and ultrasonic acoustic energy as the power source for an implantable device and the use of induced high frequency carrier currents as a vehicle for remotely determining current flow. In particular, embodiments of this disclosure include methods of sensing biochemical and biophysical characteristics of tissue by means of a miniature implanted devices powered by either microwave frequency energy or ultrasound energy. In one embodiment, a controller-transmitter may emit modulated microwave or ultrasound energy into the body to implanted receivers whereby the modulation envelope may be of a baseband frequency. Implanted receivers may convert applied energy into an electrical voltage that may be demodulated to baseband to recover the modulation envelope. This baseband voltage may be applied to tissue whereby the current flow in the tissue in response to the applied voltage may be remotely monitored and related to tissue chemical or biophysical properties. The remote detection of current flow may be achieved through envelope modulation of backscatter detected by a remote antenna, or by measuring tissue-conducted currents at either microwave, ultrasound, or baseband frequencies.

According to one embodiment, a method for adjusting tissue impedance using an implantable device may include receiving, by a wireless device implanted in a body, a modulated energy signal comprising a carrier signal and an input signal. The method may also include converting, by the implanted device, the received modulated energy signal to an electrical voltage corresponding to the input signal. The method may further include adjusting, by the implanted device, a physiologic response reflected in the impedance of tissue in contact with the implanted device by applying the electrical voltage to the tissue in contact with the implanted device.

According to another embodiment, an apparatus for adjusting a physiologic parameter such as blood flow as reflected in tissue impedance may include a receiver configured to receive a modulated energy signal comprising a carrier signal and an input signal. The apparatus may also include a demodulation circuit configured to convert the received modulated energy signal to an electrical voltage corresponding to the input signal. The apparatus may further include at least two electrodes, coupled to the demodulation circuit, configured to apply the electrical voltage to the tissue in contact with the implanted device.

According to one embodiment, a method for measuring and monitoring tissue impedance using an implantable device may include transmitting, by a wireless impedance measurement system, a modulated energy signal comprising a carrier signal and an input signal to a wireless device implanted in a body. The method may also include receiving, by the wireless impedance measurement system, an energy signal produced by tissue in response to application of a voltage to the tissue by the implanted device, wherein the voltage corresponds to the input signal and the implanted device is in contact with the tissue. The method may further include processing, by the wireless impedance measurement system, the received energy signal to determine an impedance characteristic of the tissue.

According to another embodiment, an apparatus for measuring and monitoring tissue impedance may include a signal generator configured to transmitting a modulated energy signal comprising a carrier signal and an input signal to a wireless device implanted in a body. The apparatus may also include a receiver configured to receive an energy signal produced by tissue in response to application of a voltage to the tissue by the implanted device, wherein the voltage corresponds to the input signal and the implanted device is in contact with the tissue. The apparatus may further include a signal processor configured to process the received energy signal to determine an impedance characteristic of the tissue.

According to one embodiment, a method for improved ultrasound powering of an implanted device may include sequentially, by a processor, actuating each group of ultrasound energy transmitters in an array of groups of ultrasound transmitters, wherein each group of ultrasound transmitters comprises one or more ultrasound transmitters. The method may also include monitoring, by the processor, a return signal returned from an implanted device that detected ultrasound energy from an actuated group of ultrasound transmitters. The method may further include identifying, by the processor, the return signal with the largest amplitude. The method may also include determining, by the processor, which group of ultrasound transmitters of the array of groups of ultrasound transmitters transmitted the ultrasound energy that produced the identified return signal with the largest amplitude. The method may further include selecting, by the processor, the determined group of ultrasound transmitters for emission of ultrasound energy.

According to another embodiment, a system employing improved ultrasound powering of an implanted device may include an array of groups of ultrasound energy transmitters, wherein each group of ultrasound energy transmitters comprises one or more ultrasound transmitters. The system may also include an implantable device configured to detect ultrasound energy. The system may further include a processor configured to execute the step of sequentially actuating each group of ultrasound energy transmitters in an array of groups of ultrasound transmitters, wherein each group of ultrasound transmitters comprises one or more ultrasound transmitters. The processor may also be configured to execute the step of monitoring a return signal returned from an implanted device that detected ultrasound energy from an actuated group of ultrasound transmitters. The processor may be further configured to execute the steps of identifying the return signal with the largest amplitude and determining which group of ultrasound transmitters of the array of groups of ultrasound transmitters transmitted the ultrasound energy that produced the identified return signal with the largest amplitude. The processor may also be configured to execute the step of selecting the determined group of ultrasound transmitters for emission of ultrasound energy.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments.

DETAILED DESCRIPTION

The present disclosure includes methods and apparatuses for measuring tissue impedance and monitoring PVD treatment using minimally-invasive neuro-implants with improved ultrasound powering. According to one embodiment, an implantable device may receive a high frequency carrier typically in the range of 100 kHz to several megahertz for ultrasound or alternately in the 400 MHz to 10 GHz in range for RF coupling. These carrier waves may be amplitude demodulated to produce a constant envelope voltage to electrodes at a known and/or variable frequency that is typically in the range of DC to as high as 1 MHz of in some specific cases, but may be more frequently in the range of DC to 100 kilohertz. The device may also provide a means to measure the resulting current flow, which may be accomplished in a variety of ways, in a compact device format suitable for body surface placement or invasive implantation.

For example, sensor devices for measuring impedance may be implanted into the body and may be powered by a high frequency external radio frequency (RF) or ultrasound energy envelope modulated such that the implanted sensor device reproduces the baseband voltage and applies it to tissue or to an integrated sensor in response to the envelope of the applied voltage. The current flowing through the tissue or sensor as a result of the applied voltage may create a remotely-detectable waveform that may reveal the electrical, chemical, or biophysical state of tissue. Using the remotely-detectable waveform, the tissue chemical and physical characteristics may be determined via numerous techniques, such as electrical impedance measurement, impedance spectroscopy, voltammetry, and similar electrical methods whereby a potential is applied to tissue and the resulting current flow is measured.

According to one embodiment, the sensitivity and specificity of impedance measurement techniques may be greatly increased by time-varying or sweeping the frequency of the baseband electrical potential across electrodes. This approach may allow for the use of classical techniques, such as voltammetry and electrical impedance spectroscopy, to calculate the impedance from the measurements obtained according to the embodiments of this disclosure. In the former case, a ramp waveform may be applied to the driving potential on electrodes and the current subsequently measured. Electrochemical reactions will occur at electrodes at specific redox (reduction-oxidation) potentials and the magnitude of current flow may be proportional to chemical concentration. In the latter case, the electrical potential may be swept in frequency from as low as DC to frequencies in the range of megahertz. The amplitude plot of current flow through the electrodes in this configuration as a function of frequency may be a more sensitive and specific indicator than using a single fixed voltage or current. The plot can be complex and indicative of chemical concentration, changes in physical state, or transient events occurring in tissue.

In addition to directly measuring changes in tissue impedance, the measurement of tissue or blood chemistry may be possible through recording impedance changes in two closely-spaced electrodes in contact with tissue, blood, or body fluids. In this case, there is often a membrane supporting a biochemistry through which a current is passed and whereby the system may be more responsive to a blood or tissue chemistry. According to some embodiments, the electrodes used for impedance applications may be platinum, gold, iridium, iridium oxide, silver, and the like.

In some medical conditions it may be desirable to measure tissue impedance and biochemistry continuously because the changes in these parameters reflect the course of disease or disorder that may be occurring over days or years of a person's lifetime. Likewise impedance measurement techniques have been used to monitor limb movements in rehabilitation applications and for applications in prosthetics as a control signal. Embodiments of this disclosure, such as tissue electrical impedance sensing, and the use of coupled chemical systems embodied as implantable devices, may be used for continuous monitoring of tissue electrical, physical, or chemical properties. As an example, physical sensing may be performed by monitoring the tissue electrical impedance changes with local scar tissue formation, encapsulation of an implant, and growth or decay of tissue structure.

In some embodiments, biochemical sensing may employ voltammetry that employs a cyclic change in potential with current monitoring. Biochemistries such as glucose, lactate, uric acid, and other biochemicals may be measurable. According to an embodiment, tissue impedance measured by the direct application of electrodes can reflect tissue oxygenation, blood flow, and tissue viability. In some embodiments, such devices may be used to monitor the growth of cancer, the healing of cardiac infarcts, healing wounds, and disorders of tissues, thereby providing insight into prognosis.

According to another embodiment, such trending information can be useful in adjusting therapy such as drug dosage, or monitoring lifestyle changes, such as body weight, tissue hydration changes, swelling, and progress of neuropathy. Furthermore, in some embodiments, the sensors may be implanted into a patient's body in a minimally invasive fashion such as by injection or minor surgery. Thus, embodiments of this disclosure may meet the medical need to monitor and adjust tissue electrical impedance and changes in current through chemistry systems coupled to bioelectrodes in a minimally invasive manner. Additionally, the monitored changes can be used in a feedback control method under conditions where raising the excitation levels to the implant and adjusting the modulation to achieve pulse characteristics typical of neurostimulation are sufficient of themselves to cause effects on physiologic function. In this mode the device may act not only as a sensor but as an active source of therapeutic effect. This mode of functioning between a sensor and therapeutic current flow can be achieved for example by alternation of the magnitude of the excitation applied to the implantable device. An example would be where the device is implanted near the sciatic nerve in the lower limb such that current pulses on the order of 1-10 ms long and 1-10 Hz cause vasodilation through nerve effect. As a result of the increased blood flow the tissue impedance may fall. Through an alteration of the stimulation and monitoring mode of operation, the blood flow to the lower limb can be controlled to be some preset level as required by a physician through intelligent feedback control of the applied power to the implant.

Figure 1:
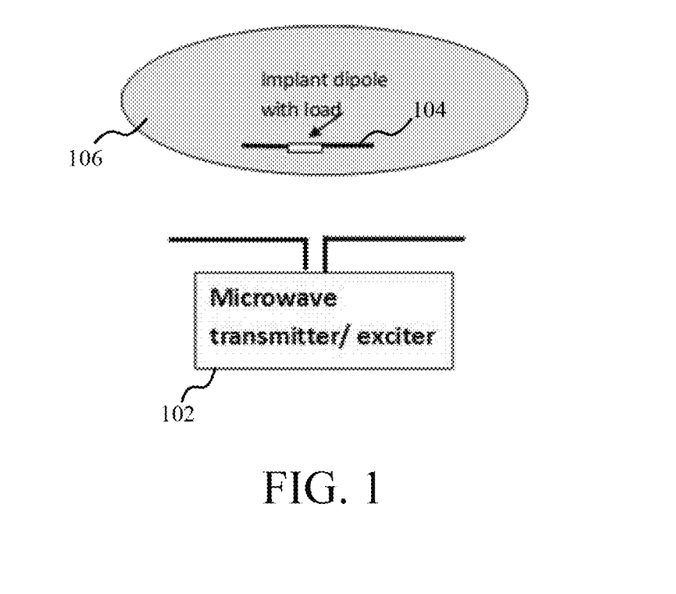
FIG. 1 is a schematic block diagram illustrating a transmitter/exciter and an implantable dipole arrangement receiver device according to one embodiment of the disclosure.

FIG. 1 illustrates a transmitter/exciter and an implantable dipole arrangement receiver device according to one embodiment of the disclosure. Referring to FIG. 1, microwave frequency electromagnetic (EM) radiation transmitted by the microwave transmitter/excitor 102 may be rectified by an implantable diode system 104 within the implant tissue 106, and the resulting half wave, full wave, or smoothed envelope may be applied to the tissue 106 by the implantable diode system 104. According to other embodiments, the implantable semiconductor diode system 104 may also be used to provide the time-varying amplitude envelope needed for tissue electrical property measurement or sensor impedance changes/adjustments.

According to an embodiment, amplitude modulation suitable for the purposes of impedance spectroscopy may be applied to a carrier wave such that neurostimulation does not occur. In some embodiments, such modulation schemes may have relatively lower amplitude than the amplitude of signals used for neurostimulation and longer pulse durations ranging into the tens of milliseconds to continuous wave. The modulation may have an impressed ramp waveform to perform, for example, voltammetry, or be swept over a range of frequencies, such as from DC to some high frequency such as a megahertz.

According to an embodiment, the current flow through the tissue 106 may be recorded by demodulating and processing the characteristics of the microwave backscatter with a computing system, such as one that includes the microwave transmitter/exciter 102. In some embodiments, the amplitude of the backscattered signal or one or more of its harmonics may be received using a microwave receiver connected to a local antenna. The resulting information obtained by amplitude demodulating the microwave backscatter signal may be used with a signal processing technique to determine relative amplitudes or changes in current amplitude as a function of the modulation applied to the microwave carrier. For example, in some embodiments, the current flowing through tissue may be proportional to the tissue impedance over the frequency range.

Figure 2:
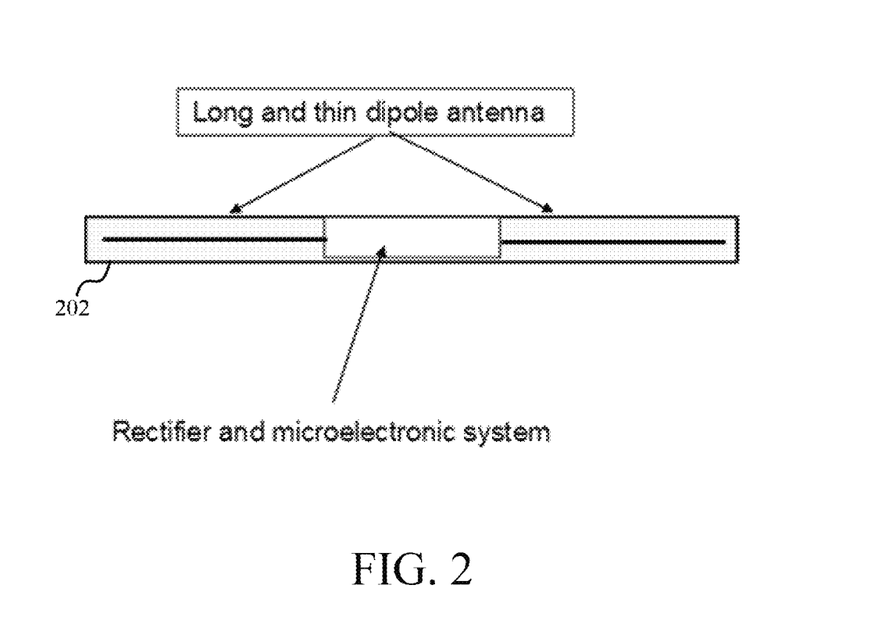
FIG. 2 is a schematic block diagram illustrating an implantable dipolar antenna receiver device with a center load according to one embodiment of the disclosure.

FIG. 2 illustrates an implantable dipolar antenna receiver device with a center load according to one embodiment of the disclosure. As shown, the implantable dipolar antenna receiver device with a center load 202, which may be the implanted portion of a sensor system, may be a high frequency diode, such as a Schottky diode, electrically connected to the center of a miniature wire dipole antenna. This antenna may be several millimeters to a centimeter or more long and made of platinum or gold or similar noble metal. The tips of the antenna wires may be exposed and have contact solution so that the antenna wire may serve a dual function of also being the interface electrode.

By way of EM induction from an antenna placed externally, the device 202 may generate a rectified voltage through the electrodes. In some embodiments, this device configuration may be loosely coupled to a microwave exciter antenna placed remotely such as on the skin. The resulting voltage applied to the tissue may present an AC frequency but otherwise constant envelope amplitude of the voltage source.

In some embodiments, the electrical configuration within the implanted semiconductor device (104 or 202) may vary so long as the device provides a suitable voltage source for electrical impedance measurements. According to an embodiment, the rectification of the incoming high microwave frequency may result in an envelope that has a lower baseband frequency envelope superposed on the half wave or full wave rectified microwave carrier. The microwave pulsation on the rectified DC envelope may be removed with an electrical filter, such as an RC low pass filter, or left as a high frequency pulsation. In some embodiments, the high frequency pulsation may have no effect on the impedance measurement made at baseband.

In some embodiments, the applied microwave carrier may be amplitude modulated by a lower frequency baseband signal. Upon rectification, the implanted diode system may present the baseband envelope signal to tissue. According to an embodiment, the current flow in tissue may produce an RF backscatter that is rich in harmonics. This harmonic signal may be detected by a remote antenna or by body surface electrode couplings. Through the detection and demodulation of the current flow, the absolute or relative tissue impedance change with frequency can be determined.

In some embodiments, electrical energy may be harvested by coupling a semiconducting rectifier system, such as a Schottky diode, that both rectifies the current for application to implanted electronic devices (104 or 202) and directly powers neurostimulation pulses applied to tissue. In some embodiments, capacitive coupling to the electrodes may be employed to ensure a charge balance. According to other embodiments, the implant (104 or 202) may also incorporate voltage limiters or other safety devices to prevent shock or unwanted effects in tissue resulting from high current flows.

According to an embodiment, in systems where power is transferred across the body tissue to a passive receiver, the efficiency of the energy transfer can vary due to small changes in coupling of the outside exciter antenna. In some embodiments, this variation may be less important in the overall functionality of this impedance measuring technique because the important aspect may be the relative shape of the current flow time history as a function of the modulation voltage. According to some embodiments, a plot of the current versus applied voltage may be significant for illustrating the plot feature relationships with respect to each other. Thus, a signal processing technique can be applied to the current vs modulation frequency data whereby the amplitude of the waveform may be normalized around some feature, which may be the highest or lowest applied frequency, and then changes in waveform shape may be determined from nominal and then related to the impedance change.

Figure 3:
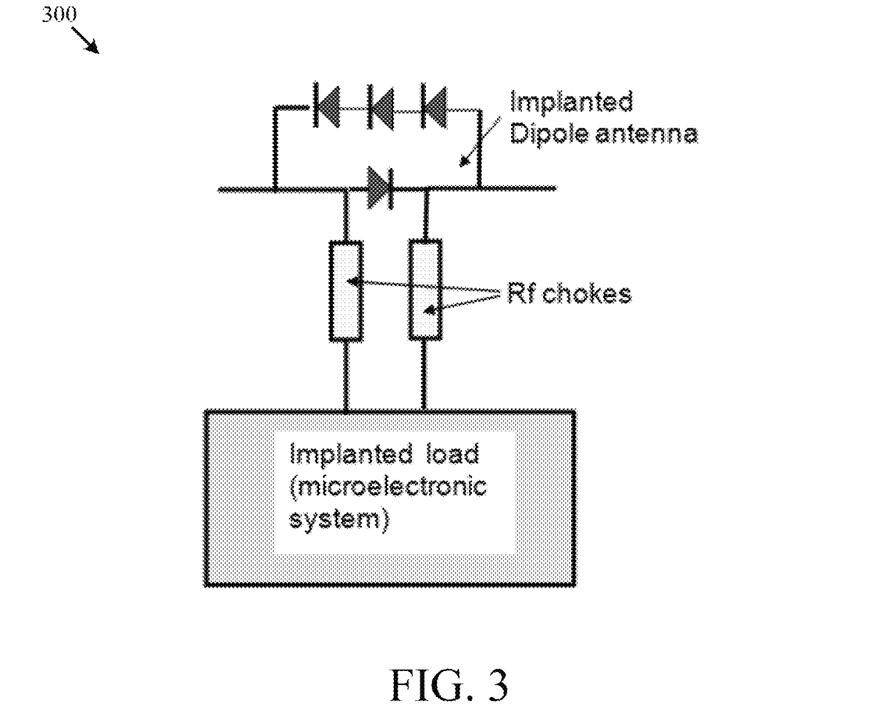
FIG. 3 is a schematic block diagram illustrating an implantable energy harvesting system employing an optional rectifier and employing an isolating choke to the load according to one embodiment of the disclosure.

In some embodiments, the implantable medical impedance monitoring technology can employ aspects of safety, pulse-width modulation, and feedback control over implanted device current. In short, safety considerations may require that the current driven by an implanted device be limited so that if for some reason the coupling were to momentarily increase, for example, a sudden change in position on an external antenna, or some environmental source of high RF intensity were applied, that currents would not be induced to high levels. Thus, a microwave limiting diode, such as a zener diode placed across the antenna rectifying diode, or a similar voltage limiting diode placed after a low pass filter to remove the microwave component and leave only the integrated pulse envelope, may be used to limit the current induced in tissue. As an example, FIG. 3 illustrates an implanted energy harvesting system 300 employing an optional rectifier and employing an isolating choke to the load according to one embodiment of the disclosure. Also described in related applications are the use of pulse width control to achieve the variation in average power that allows for defining of the average modulation waveform shape, and the use of capacitive coupling to electrodes.

According to another embodiment, ultrasound may be used in which ultrasound energy is applied to the body surface and then its directed energy harvested by a miniature implanted piezoelectric element. That is, the implanted device of this embodiment may apply ultrasound energy in the medical diagnostic range to tissue and harvest the energy to produce neurostimulation. Such devices may be sufficiently small so as to be able to pass through the lumen of a syringe needle and hence be introduced into tissue by minimally invasive means. In some embodiments of this disclosure, the device may be used with the added inclusion of methods of current limiting, pulse width modulation, and feedback control.

Figure 4:
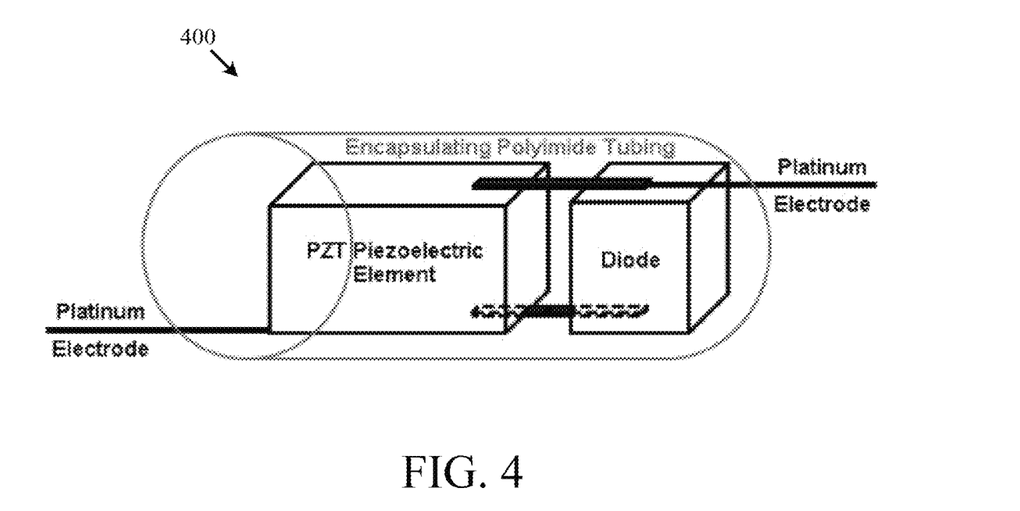
FIG. 4 is a schematic block diagram illustrating the assembly of components of an implantable neurostimulator with the diode in parallel with a piezoelectric PZT-5A ceramic according to one embodiment of the disclosure.

In one embodiments, an implantable neurostimulator, such as the aforementioned miniature implanted piezoelectric element, may be constructed using a microscope to assemble the electronic components and then inserted and encapsulated in 1.3 mm diameter polyimide tubing. For example, FIG. 4 illustrates the assembly of components of an implantable neurostimulator 400 with the diode in parallel with a piezoelectric PZT-5A ceramic according to one embodiment of the disclosure. Components of the device 400 may be interconnected with conductive silver epoxy to a rectifier and two wire-type Pt electrodes. The Schottky diode may have a low threshold voltage and a small SC-79 package. In some embodiments, the device 400 may be encapsulated in medical grade epoxy (353ND, Epoxy Technology).

In some embodiments, the modulation of the currents generated are such that they avoid neurostimulation and rather present an output electrical waveform suited to impedance measurement as described above. The piezoelectric element within the implant may generate an alternating current that is then rectified and applied to implant electrodes. According to an embodiment, the emission from an ultrasound transducer may be amplitude modulated according to the strategies outlined above and according to the needs of the electrode system and method used to determine electrode sensor or tissue impedance. According to some embodiments, this modulation that avoids neurostimulation may be, for example, a tone burst whereby the ultrasound envelope is modulated at baseband by a swept frequency that extends from DC to a hundred kilohertz or more. Biopotential electrodes or a loop antenna placed on the body surface may detect a signal as a result of the current passing through the electrodes into tissue. Current flow through tissue may produce an EM wave at the ultrasound frequency and this wave may be remotely detectable. Its amplitude may be demodulated and related to current flow by signal processing based on pre-calibration or modulation waveform shape discrimination based on frequency as discussed above.

A characteristic of ultrasound compared to EM radiation is the existence of an acoustic transit time delay. Thus, the application of short pulses of ultrasound, on the order of 1-5 microseconds may result in a delayed electrical response from the implant that obviates the potential interference in detection of the resulting tissue current by the ultrasound transmitter. However, as in the case of pulse width modulation for the generation of a varying amplitude-integrated current, the electrochemistry at the electrode system may not see the high frequency component and instead respond to the envelope average value.

Determination of the tissue current flow as required to make impedance measurements may result from using body surface contacting bioelectrodes to record high frequency potentials that are volume-conducted to the skin from the implant-generated currents. These may primarily exist as variations of the amplitude of typically megahertz frequency ultrasound at the envelope baseband frequency. According to some embodiments, these may also be demodulated by conventional techniques in order to recover the trend of the amplitude modulation.

According to another embodiment, the methods and apparatuses disclosed herein may be used for monitoring PVD treatment. For example, wireless micro devices powered by microwave or ultrasound energy may be fabricated to measure and telemeter tissue impedance spectrums for applications in PVD treatment monitoring. In some embodiments, the system may be characterized by simplicity of the implant consisting of only two electrical components. According to an embodiment, Ex vivo testing may show the potential for constructing tissue impedance spectrum plots over the range from 10 Hz to 10 kHz by a device less than 1 mm in diameter and 1 cm long. In some embodiments, the neurostimulator micro device (such as 104, 202, 300, or 400) may be powered by a continuous waveform 650 kHz ultrasound with a swept-frequency amplitude modulation. The system may be operated at safe ultrasound power levels on the order of 10-100 mW/cm2. The device may prove to be sensitive and able to measure tissue impedances over a broad range. Volume-conducted signals carrying impedance information from the microdevice may be remotely detected by surface biopotential electrodes.

According to an embodiment of this disclosure, tissue impedance monitoring may be realized via a minimally invasive approach using a microelectronic device that can locally measure the tissue impedance spectrum and telemeter the information to the body surface. In some embodiments, the impedance measurement function of a microelectronic device may be combined with peripheral limb neurostimulation performed by microwave- or ultrasound-powered microelectronic devices to cause vasodilation in order to improve blood flow and for relief of pain. Accordingly, in one embodiment, a micro device as disclosed herein may be used to monitor the effect of interventions through impedance measurements by a device small enough to be introduced through injection. Devices of small size have the advantage of avoiding silicone lead wires tunneled under the skin or through tissues.

In some embodiments, the micro devices disclosed herein may be used to measure the magnitude and phase of tissue impedances. This approach may employ ultrasound energy to the device to provide energy to create the needed frequency-swept wave that interrogates tissue impedance as well as uses volume conduction for communication to an external receiver.

In some embodiments, a system using a neurostimulator (such as 104, 202, 300, or 400) to perform tissue impedance measurements may include a modulation signal generator, carrier signal generator, amplifier, lock-in amplifier, and a commercial focused ultrasound transducer with a center frequency of 650 kHz and diameter of 50 mm. In some embodiments, the carrier signal generator may provide a high frequency sinusoidal signal at 650 kHz required to power an ultrasound transducer while the modulation signal generator outputs a low frequency (in the range of 10 Hz up to 10 kHz) sinusoidal signal. This low frequency signal may be used to modulate the high frequency carrier, which then through the amplifier can be applied to the transducer. The transducer may reproduce the same AM modulated signal in acoustic form, which may then be applied to the implant. The PZT crystal of the device may then generate an AM modulated waveform in the form of an electrical signal because it follows the external driving waveform. Next, the diode of the neurostimulator may rectify (demodulate) the AM signal, thereby causing the tissue to see the varying lower frequency modulation signal. The magnitude of the current passing through the tissue may then dependent on the tissue impedance at the modulation frequency. The skin potential from the device current flow may be remotely detected by bioelectrodes and its amplitude and phase may be recorded as a function of ultrasound modulation frequency.

Figure 5:
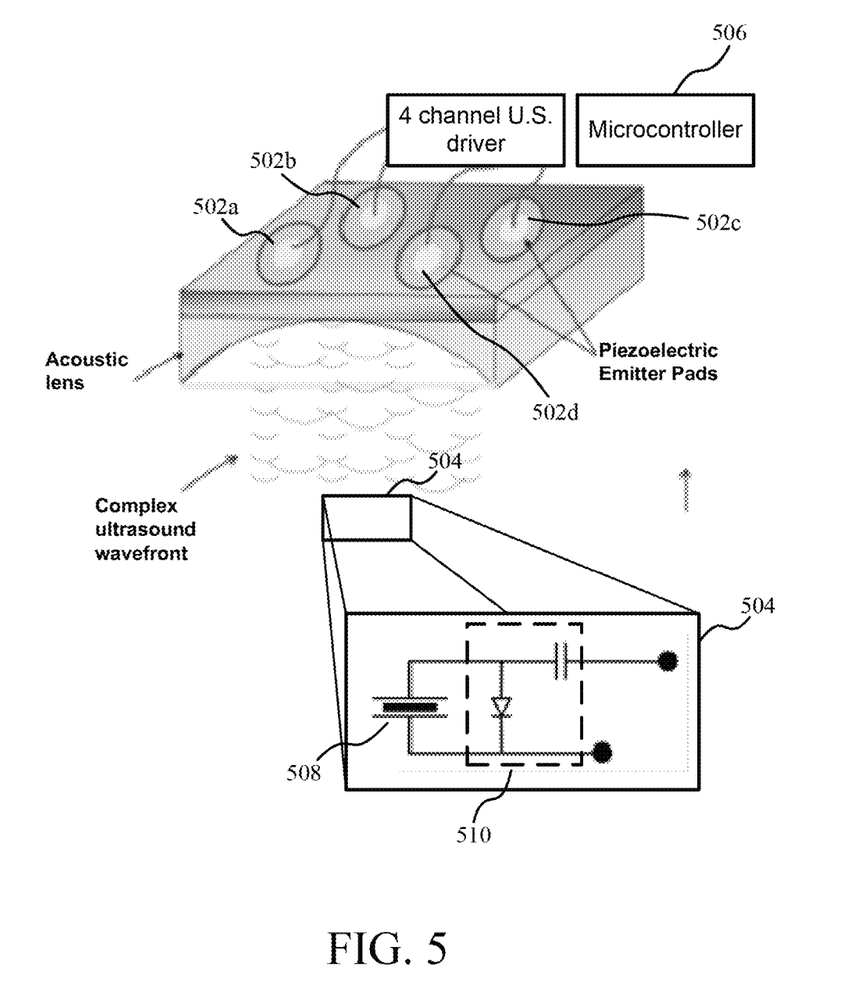
FIG. 5 is a schematic block diagram illustrating a system for improved ultrasound powering of an implanted device according to one embodiment of the disclosure.

FIG. 5 is a schematic block diagram illustrating a system for improved ultrasound powering of an implanted device according to one embodiment of the disclosure. In some embodiments, the system illustrated in FIG. 5 may improve the coupling of ultrasound energy to powered implants in order to reduce sensitivity of the external unit positioning when shifts occur, for example, due to patient movement. As show in the embodiment of FIG. 5, improved power delivery to ultrasound-powered neurostimulator implants may be achieved by means of feedback from implant generated currents by way of electrodes placed on the body surface over the implant.

Ultrasonic transcutaneous energy transfer (UTES), such as that illustrated in FIG. 5, may have significant advantages lending to suitable use for powering implantable devices. In some embodiments, the efficiency of ultrasound powered neurostimulation may primarily depend on the accurate focusing of the ultrasound beam onto the implant for maximum energy transfer. In the embodiment illustrated in FIG. 5, multiple transducer ultrasonic applicators may be used to adjust the beam directivity by way of a feedback control system so as to select one of a group of transducers that provide the highest implant power transfer.

For example, as illustrated in the embodiment of FIG. 5, a microcontroller 506 may be configured with a software program to sequentially actuate multiple ultrasound emitter groups 502a-502d. In some embodiments, the size of an ultrasound emitter, such as emitter 502a, may be on the order of 1 cm diameter although it can generally be of any size. In some embodiments, the emitters 502a-502d may be placed as an array on the body surface over an implant 504. As was illustrated in FIG. 4, the implant 504 may include a piezoelectric material 508 and a demodulation diode circuit 510. A body surface unit, such as one including the emitters 502a-502d, coupled to the micontroller 506 may electrically monitor the implant signal returned by the implant 504 when each emitter 502a-502d is actuated. From the amplitude of the ultrasound-evoked returned signal the microcontroller 506 may determine which one or combination of ultrasound emitters 502a-502d produce the highest implant output consistent with tolerable battery power drains within the emitter electronic system. This emitter selection process may be periodically re-evaluated by the microcontroller 506, perhaps as frequently as every few seconds to every few hours. In some embodiments, the re-evaluation may keep the implant 504 powered most effectively by selecting the ultrasound transducer 502a-502d best positioned to couple to the implant as the emitting transducer. In embodiments in which the implanted devices are widely separated, multiple ultrasound transducers may be used to transfer energy to individual devices. In addition, in embodiments where ultrasound energy is dispersed nonuniformly, implanted ultrasound devices may operate in a voltage limited mode and multiple devices may provide known and uniform voltages and currents.

In view of exemplary systems shown and described herein, methodologies that may be implemented in accordance with the disclosed subject matter will be better appreciated with reference to various functional block diagrams. While, for purposes of simplicity of explanation, methodologies are shown and described as a series of acts/blocks, it is to be understood and appreciated that the claimed subject matter is not limited by the number or order of blocks, as some blocks may occur in different orders and/or at substantially the same time with other blocks from what is depicted and described herein. Moreover, not all illustrated blocks may be required to implement methodologies described herein. It is to be appreciated that functionality associated with blocks may be implemented by software, hardware, a combination thereof or any other suitable means (e.g. device, system, process, or component). Additionally, it should be further appreciated that methodologies disclosed throughout this specification are capable of being stored on an article of manufacture to facilitate transporting and transferring such methodologies to various devices. Those skilled in the art will understand and appreciate that a methodology could alternatively be represented as a series of interrelated states or events, such as in a state diagram.

Figure 6:
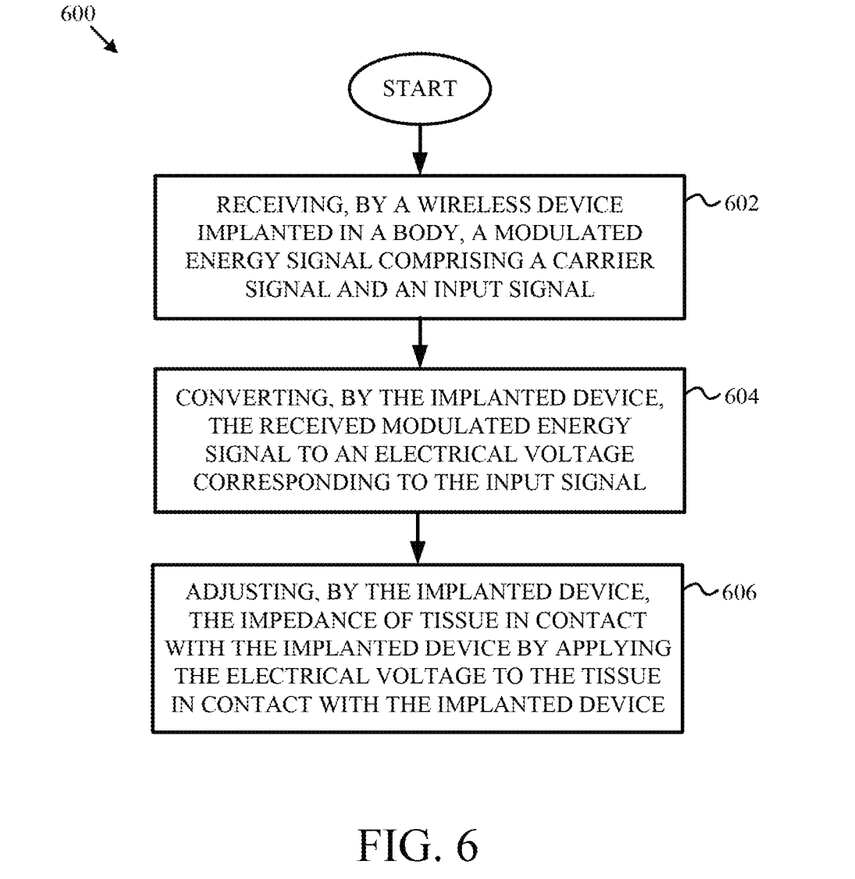
FIG. 6 is a flow chart illustrating a method for adjusting tissue impedance using an implantable device according to one embodiment of the disclosure.

FIG. 6 is a flow chart illustrating a method for adjusting tissue impedance using an implantable device according to one embodiment of the disclosure. It is noted that embodiments of method 600 may be implemented with the systems described with respect to FIGS. 1-5. Specifically, method 600 includes, at block 602, receiving, by a wireless device implanted in a body, a modulated energy signal comprising a carrier signal and an input signal. In some embodiments, the modulated energy signal may be a microwave energy signal, while in other embodiments the modulated energy signal may be an ultrasound energy signal.

At block 604, method 600 includes converting, by the implanted device, the received modulated energy signal to an electrical voltage corresponding to the input signal. In some embodiments, converting may include demodulating the received modulated energy signal with an envelope detector.

At block 606, method 600 includes adjusting, by the implanted device, the impedance of tissue in contact with the implanted device by applying the electrical voltage to the tissue in contact with the implanted device. In some embodiments, to determine the specificity and sensitivity of the tissue in response to application of electrical voltage based on the input signal, the input signal may be varied to identify.

Figure 7:
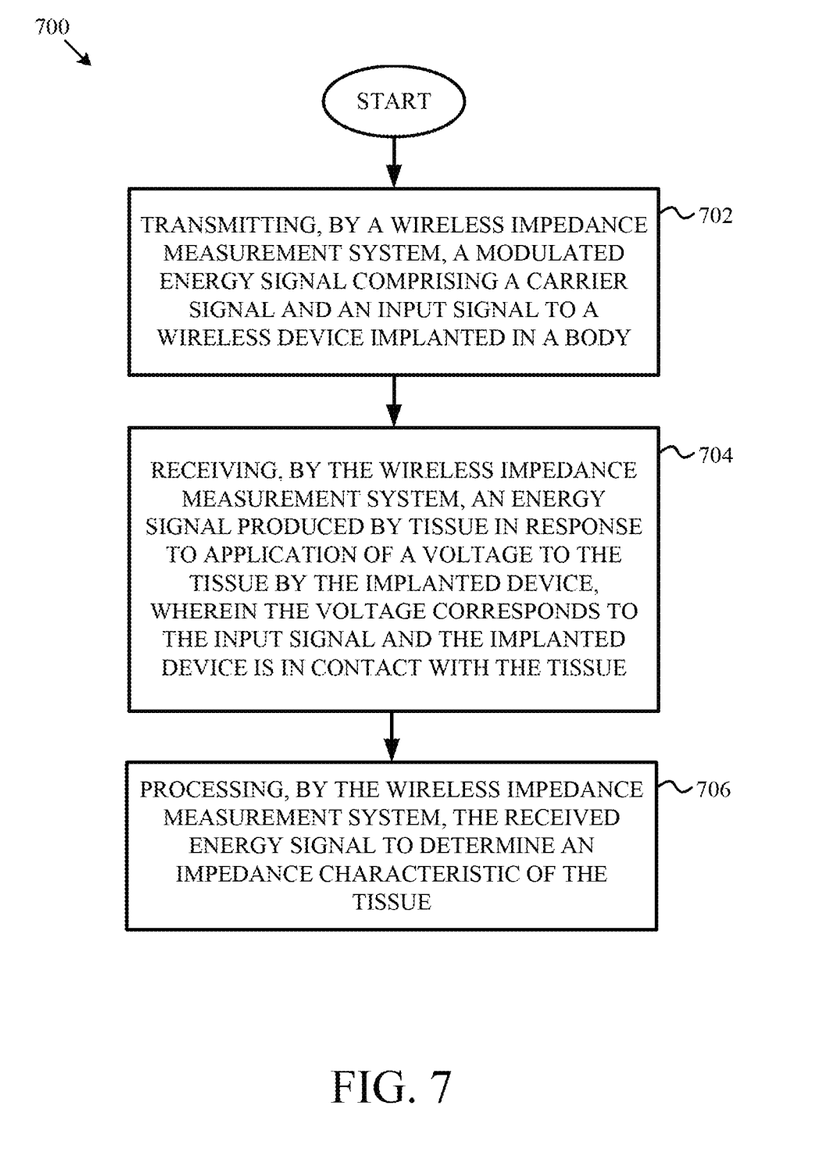
FIG. 7 is a flow chart illustrating a method for measuring and monitoring tissue impedance using an implantable device according to one embodiment of the disclosure.

FIG. 7 is a flow chart illustrating a method for measuring and monitoring tissue impedance using an implantable device according to one embodiment of the disclosure. It is noted that embodiments of method 700 may be implemented with the systems described with respect to FIGS. 1-5. Specifically, method 700 includes, at block 702, transmitting, by a wireless impedance measurement system, a modulated energy signal comprising a carrier signal and an input signal to a wireless device implanted in a body. In some embodiments, transmitting may include transmitting a modulated microwave energy signal, while in other embodiments transmitting may include transmitting a modulated ultrasound energy signal.

At block 704, method 700 includes receiving, by the wireless impedance measurement system, an energy signal produced by tissue in response to application of a voltage to the tissue by the implanted device, wherein the voltage corresponds to the input signal and the implanted device is in contact with the tissue. In some embodiments, receiving may include detecting a backscattered microwave energy signal with a microwave receiver. In other embodiments, receiving may also include detecting current in the tissue with at least one of a biopotential electrode and body surface antenna.

At block 706, method 700 includes processing, by the wireless impedance measurement system, the received energy signal to determine an impedance characteristic of the tissue. In some embodiments, processing may include determining a relationship between a change in the input signal and a change in the tissue impedance.

Figure 8:
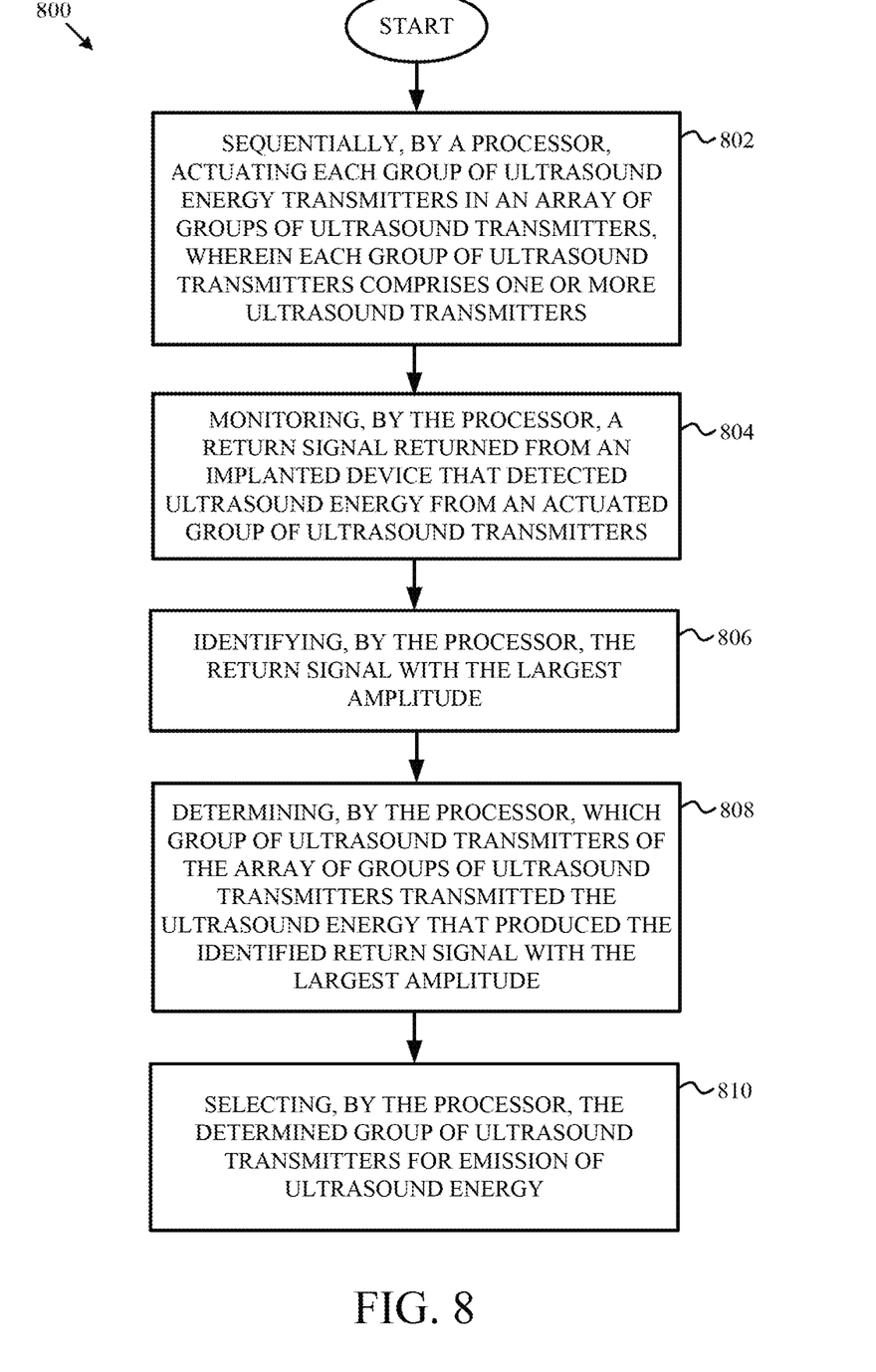
FIG. 8 is a flow chart illustrating a method for improved ultrasound powering of an implanted device according to one embodiment of the disclosure.

FIG. 8 is a flow chart illustrating a method for improved ultrasound powering of an implanted device according to one embodiment of the disclosure. It is noted that embodiments of method 800 may be implemented with the systems described with respect to FIGS. 1-5. Specifically, method 800 includes, at block 802, sequentially, by a processor, actuating each group of ultrasound energy transmitters in an array of groups of ultrasound transmitters, wherein each group of ultrasound transmitters comprises one or more ultrasound transmitters. In some embodiments, the array of groups of ultrasound transmitters may be placed on a body surface over the implant.

At block 804, method 800 includes monitoring, by the processor, a return signal returned from an implanted device that detected ultrasound energy from an actuated group of ultrasound transmitters. At block 806, method 800 includes identifying, by the processor, the return signal with the largest amplitude. At block 808, method 800 includes determining, by the processor, which group of ultrasound transmitters of the array of groups of ultrasound transmitters transmitted the ultrasound energy that produced the identified return signal with the largest amplitude. In some embodiments, a user may be presented with a visual display or audible feedback of the returned signal indicating when the current in the implanted device was actively flowing within specified parameters so that the user can determine which group of ultrasound transmitters of the array of groups of transmitters transmitted the ultrasound energy that produced the identified return signal. At block 810, method 800 includes selecting, by the processor, the determined group of ultrasound transmitters for emission of ultrasound energy. In some embodiments, one or more steps performed at block 802-810 may be performed periodically in time.

The schematic flow chart diagrams of FIGS. 6-8 are generally set forth as a logical flow chart diagrams. As such, the depicted order and labeled steps are indicative of aspects of the disclosed methods. Other steps and methods may be conceived that are equivalent in function, logic, or effect to one or more steps, or portions thereof, of the illustrated methods. Additionally, the format and symbols employed are provided to explain the logical steps of the methods and are understood not to limit the scope of the methods. Although various arrow types and line types may be employed in the flow chart diagrams, they are understood not to limit the scope of the corresponding methods. Indeed, some arrows or other connectors may be used to indicate only the logical flow of the methods. For instance, an arrow may indicate a waiting or monitoring period of unspecified duration between enumerated steps of the depicted methods. Additionally, the order in which a particular method occurs may or may not strictly adhere to the order of the corresponding steps shown.

If implemented in firmware and/or software, the functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and blu-ray discs. Generally, disks reproduce data magnetically, and discs reproduce data optically. Combinations of the above should also be included within the scope of computer-readable media.

In addition to storage on computer-readable medium, instructions and/or data may be provided as signals on transmission media included in a communication apparatus. For example, a communication apparatus may include a transceiver having signals indicative of instructions and data. The instructions and data may be configured to cause one or more processors to implement the functions outlined in the claims.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for measuring and monitoring tissue impedance using an implantable device, comprising:
    transmitting, by a wireless impedance measurement system, a first modulated ultrasound energy signal comprising a carrier signal and an input signal to a wireless device implanted in a body;
    receiving, by the wireless impedance measurement system, an energy signal produced by tissue in response to application of a voltage to the tissue by the implanted device, wherein the voltage corresponds to the input signal and the implanted device is in contact with the tissue; and
    processing, by the wireless impedance measurement system, the received energy signal to determine an impedance characteristic of the tissue and monitor peripheral vascular disease (PVD) treatment.

2. The method of claim 1, wherein processing comprises determining a relationship between a change in the input signal and a change in the tissue impedance.

3. The method of claim 1, wherein receiving comprises detecting current in the tissue with a biopotential electrode and/or a body surface antenna.

4. The method of claim 1, further defined as a method for adjusting tissue impedance using the implantable device, comprising:
    receiving, by the wireless device implanted in the body, a second modulated ultrasound energy signal comprising a carrier signal and an input signal;
    converting, by the implanted device, the received second modulated ultrasound energy signal to an electrical voltage corresponding to the input signal; and
    adjusting, by the implanted device, the impedance of tissue in contact with the implanted device by applying the electrical voltage to the tissue in contact with the implanted device.

5. The method of claim 4, wherein converting comprises demodulating the received second modulated ultrasound energy signal with an envelope detector.

6. The method of claim 4, wherein the input signal is varied to identify a response sensitivity of the tissue to the input signal.

7. An apparatus for measuring and monitoring tissue impedance, comprising:

an ultrasound signal generator configured to transmitting transmit a modulated ultrasound energy signal comprising a carrier signal and an input signal to a wireless device implanted in a body;

a first receiver configured to receive an energy signal produced by tissue in response to application of a voltage to the tissue by the implanted device, wherein the voltage corresponds to the input signal and the implanted device is in contact with the tissue; and a signal processor configured to process the received energy signal to determine an impedance characteristic of the tissue and to monitor peripheral vascular disease (PVD) treatment.

8. The apparatus of claim 7, wherein the receiver comprises a biopotential electrode and/or a body surface antenna to detect current in the tissue, and wherein the processor is configured to determine a relationship between a change in the input signal and a change in the tissue impedance.

9. The apparatus of claim 7, wherein the receiver comprises a biopotential electrode.

10. The apparatus of claim 9, wherein the biopotential electrode comprises iridium oxide.

11. The apparatus of claim 9, wherein the receiver further comprises a body surface antenna configured to detect current in the tissue.

12. The apparatus of claim 7, wherein the wireless device comprises, a second receiver which is configured to receive the modulated ultrasound energy signal comprising the carrier signal and the input signal;

a demodulation circuit, coupled to a wire dipole antenna, configured to convert the received modulated ultrasound energy signal to an electrical voltage corresponding to the input signal; and at least two electrodes, coupled to the demodulation circuit, configured to apply the electrical voltage to the tissue in contact with the implanted device.

13. The apparatus of claim 12, wherein the second receiver comprises a piezoelectric material configured to detect ultrasound energy.

14. The apparatus of claim 5, further comprising:

a voltage limiter configured to limit the voltage available across the at least two electrodes; and wherein the demodulation circuit comprises an envelope detector.

\* \* \* \* \*